United States Patent [19]

Plöger et al.

[11] 4,006,182
[45] Feb. 1, 1977

[54] PROCESS FOR THE PREPARATION OF 1-AMINOALKANE-1,1-DIPHOSPHONIC ACIDS

[75] Inventors: Walter Plöger, Hilden; Norbert Schindler, Monheim-Baumberg; Karl-Heinz Worms, Dusseldorf-Holthausen, all of Germany

[73] Assignee: Henkel & Cie G.m.b.H., Dusseldorf-Holthausen, Germany

[22] Filed: Mar. 16, 1972

[21] Appl. No.: 235,838

[30] Foreign Application Priority Data

Mar. 31, 1971 Germany .......................... 2115737

[52] U.S. Cl. ............................. 260/502.5; 252/8.8; 252/180; 260/290 R; 260/501.12
[51] Int. Cl.² ............................................ C07F 9/38
[58] Field of Search .................................. 260/502.5

[56] References Cited

UNITED STATES PATENTS

| | | | |
|---|---|---|---|
| 3,549,728 | 12/1970 | Balde et al. ..................... | 260/502.5 |
| 3,565,949 | 2/1971 | Cummins ......................... | 260/502.5 |
| 3,668,138 | 6/1972 | Hoover et al. ................... | 260/502.5 |

FOREIGN PATENTS OR APPLICATIONS

| | | | |
|---|---|---|---|
| 1,002,355 | 2/1957 | Germany ......................... | 260/502.5 |
| 6,407,908 | 1/1965 | Netherlands ..................... | 260/502.5 |
| 995,462 | 6/1965 | United Kingdom ............. | 260/502.5 |

OTHER PUBLICATIONS

Wagner et al., "Synthetic Organic Chemistry", (1953), pp. 565,566,567,570

Primary Examiner—Joseph E. Evans
Attorney, Agent, or Firm—Hammond & Littell

[57] ABSTRACT

Process for the preparation of 1-aminoalkane-1,1-diphosphonic acids of the formula

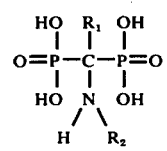

in which $R_1$ represents a member selected from the group consisting of alkyl with 1 to 20 carbon atoms, phenyl, phenylalkyl with 7 to 12 carbon atoms, alkylphenyl with 7 to 12 carbon atoms, and in which $R_2$ represents a member selected from the group consisting of hydrogen and alkyl with 1 to 4 carbon atoms, consisting essentially of reacting adducts of a hydrogen halide selected from the group consisting of HCl and HBr to a corresponding carboxylic acid amide of the formula

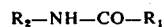

wherein $R_1$ and $R_2$ have the above-assigned meanings, with phosphorus acid; and recovering said 1-aminoalkane-1,1-diphosphonic acids.

4 Claims, No Drawings

PROCESS FOR THE PREPARATION OF 1-AMINOALKANE-1,1-DIPHOSPHONIC ACIDS

PRIOR ART

The invention relates to a novel process for the preparation of 1-aminoalkane-1,1-diphosphonic acids, whose amino group can optionally be substituted.

In the prior art it is known to prepare 1-aminoalkane-1,1-diphosphonic acids by reacting a nitrile with a phosphorus trihalide and then treating the reaction mixture with water. The reaction can also be conducted in the presence of organic acids or their anhydrides or in the presence of an inorganic oxygen containing acid. This known method has the disadvantage that satisfactory yields are only obtained with the use of phosphorus tribromide. In addition it is not possible by this process to prepare compounds in which the hydrogen atoms of the amino group are replaced, for instance, by alkyl residues.

It is also known in the prior art to prepare N,N-dimethyl-1-aminomethane-1,1-diphosphonic acid tetraethyl ester by the reaction of dimethylformamidodiacetal with diethyl phosphite. This process is complicated, especially since the esters still have to be converted into the free acids.

OBJECTS OF THE INVENTION

It is an object of the present invention to provide an improvement which will overcome all of the above state disadvantages of the prior art.

It is a further object of the present invention to provide a process for the preparation of 1-aminoalkane-1,1-diphosphonic acids of the formula

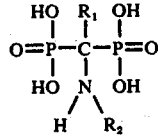

in which $R_1$ represents a member selected from the group consisting of alkyl with 1 to 20 carbon atoms, phenyl, phenylalkyl with 7 to 12 carbon atoms, alkylphenyl with 7 to 12 carbon atoms, and in which $R_2$ represents a member selected from the group consisting of hydrogen and alkyl with 1 to 4 carbon atoms, consisting essentially of reacting adducts of a hydrogen halide selected from the group consisting of HCl and HBr to a corresponding carboxylic acid amide of the formula

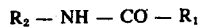

wherein $R_1$ and $R_2$ have the above-assigned meanings, with phosphorus acid; and recovering said 1-aminoalkane-1,1-diphosphonic acids.

These and other objects of the present invention will become apparent as the description thereof proceeds.

DESCRIPTION OF THE INVENTION

The present invention is directed to a process for the preparation of 1-aminoalkane-1,1-diphosphonic acids of the formula

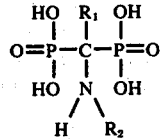

in which $R_1$ represents a member selected from the group consisting of alkyl with 1 to 20 carbon atoms, phenyl, phenylalkyl with 7 to 12 carbon atoms, alkylphenyl with 7 to 12 carbon atoms, and in which $R_2$ represents a member selected from the group consisting of hydrogen and alkyl with 1 to 4 carbon atoms, consisting essentially of reacting adducts of a hydrogen halide selected from the group consisting of HCl and HBr to a corresponding carboxylic acid amide of the formula

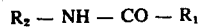

wherein $R_1$ and $R_2$ have the above-assigned meanings, with phosphorus acid; and recovering said 1-aminoalkane-1,1-diphosphonic acids.

It is to be understood that adducts of hydrogen chloride or hydrogen bromide to carboxylic acid amides refer to carboxylic acid amide hydrochlorides or hydrobromides, which correspond generally to the formula $R_1CONHR_2 \cdot HX (X = Cl, Br)$. However this definition also includes those hydrohalo derivatives of carboxylic acid amides whose composition deviates from a 1:1 molar ratio of acid amide to hydrogen halide, such as the acetamide hydrobromide of the formula $CH_3CONH_2 \cdot 0.5\ HBr$. Examples of carboxylic acid amides used as starting material for the amide component of the hydrogen halide adducts thereto include the following compounds: acetamide, propionic acid amide, butyric acid amide, valeric acid amide, caprylic acid amide, lauric acid amide, palmitic acid amide, stearic acid amide, isobutyric acid amide, hydrocinnamic acid amide, N-methylacetamide, N-ethylpropionic acid amide, N-propylisovaleric acid amide and N-isopropylcapronic acid amide.

It is preferred to react the adducts of hydrogen chloride or hydrogen bromide and carboxylic acid amides with phosphorous acid in such amounts, that the molar ratio of carboxylic acid amide to phosphorous acid lies in the range of from 1:0.5 to 1:3.

The reaction is usually carried out at temperatures ranging from 100° to 170° C, preferably from 140° to 160° C. In order for the reaction to take place it is only necessary to heat a mixture of the starting components to this temperature range, generally without the use of a solvent, and subsequently to maintain the reaction mixture for a sufficient period of time in this temperature range. The reaction time at a given reaction temperature depends to a certain degree upon the acid amide component used and the time can range from 1 to 10 hours.

As an alternative embodiment of the process of the invention the adducts from hydrogen chloride or hydrogen bromide and carboxylic acid amides are not used as starting material. Instead they are prepared in a mixture of carboxylic acid amide and phosphorous acid by introduction of hydrogen halide gas into this mixture.

The processing of the reaction mixture can then be carried out by the addition of a corresponding amount of water. This causes the 1-aminoalkane-1,1-diphosphonic acids with a longer hydrocarbon residue $R_1$ to immediately precipitate out of the aqueous solution because of their lower solubility. The precipitate can be separated by filtration. The 1-aminoalkane-1,1-diphosphonic acids with short hydrocarbon residues can be precipitated from the aqueous solution by the addition of suitable water miscible organic solvents, such as acetone, lower alcohols or mixtures of acetone and ethyl acetate. Before the precipitation with organic solvents it has been found to be advantageous to lead steam through the reaction mixture, to be worked up, until the distillate therefrom is no longer acidic. In this way volatile components, such as hydrogen chloride or hydrogen bromide are expelled from the aqueous solution. Furthermore, the aqueous solutions of the 1-aminoalkane-1,1-diphosphonic acids can be treated, before the precipitation with organic solvents, with cationic exchange resins, in order to obtain particularly pure products.

Steam distillation and cation exchange can also be used as purification procedures when the obtained aqueous solution is to be used directly as a technical product.

The 1-aminoalkane-1,1-diphosphonic acid products can be converted to the salts by the addition of equivalent amounts or respective bases as desired in each case. There can be a stepwise or a complete neutralization of the phosphonic acid groups. Of particular interest are the water soluble alkali metal salts and the ammonium salts. They can be prepared by reaction of the phosphonic acids with NaOH, KOH, $K_2CO_3$, $Na_2CO_3$ or $NH_3$. According to the amount of salt utilized in each instance the corresponding mono-, di-, tri- and tetraalkali diphosphonates or ammonium diphosphonates are obtained. The 1-aminoalkane-1,1-diphosphonic acids also form corresponding salts with amine bases. Suitable amine bases are mono, di- and trialkanolamines, particularly those with 1 to 4 carbon atoms in the alkanol residue. Other suitable amine bases include pyridine and guanidine. In each instance the reaction is conducted by known methods.

By the described process it is possible to prepare in a simple way 1-aminoalkane-1,1-diphosphonic acids, in which the amino group may optionally be substituted, or their salts. These compounds may be utilized as sequestering agents in many technical applications. They may, for example, be used for water softening, in cleaning processes, particularly in bottle cleaning or also for descaling of fabrics in washing processes. They are further suitable as additions to dye baths for textiles, in order to bind metal ions, which would otherwise cause undesirable color shades in the textiles.

In certain cases it is advantageous to use mixtures of the 1-aminoalkane-1,1-diphosphonic acids with other sequestering agents, such as aminotriacetic acid, polyamino polycarboxylic acids and condensed phosphates. Of these other sequestering agents either individuals or mixtures can be used with the diphosphonic acids of this invention.

The following examples are merely illustrative of the present invention and are not to be deemed limitative in any manner thereof.

EXAMPLE 1

A mixture of 95.6 gm of acetamide hydrochloride and 82 gm of phosphorous acid was stirred for 3 hours at a temperature of 155°–160° C. Subsequently steam was led through the reaction mixture until the distillate no longer was acidic. The residue of the steam distillation was treated with a cationic exchange resin in the H-form. The eluate was concentrated and the 1-aminoethane-1,1-diphosphonic acid was precipitated by the addition of acetone. The acid was filtered off and dried. The yield was 25.3 gm.

EXAMPLE 2

A mixture of 95.6 gm of acetamide hydrochloride and 164 gm of phosphorous acid was stirred for 3 hours at a temperature of 155°–160° C. The 1-aminoethane-1,1-diphosphonic acid reaction product was isolated and purified by working up the reaction mixture analogously to Example 1. The yield was 26.1 gm.

EXAMPLE 3

99.5 gm of an adduct of 2 mols of acetamide and 1 mol of hydrogen bromide were mixed with 84.5 gm of phosphorous acid, and the mixture was heated for 5 hours at a temperature of 150°–160° C. The 1-aminoethane-1,1-diphosphonic acid reaction product was isolated and purified, as described in Example 1. The yield was 45 gm.

EXAMPLE 4

Into a mixture of 59 gm of acetamide and 82 gm of phosphorous acid, hydrogen chloride gas was introduced therein for a period of 3 hours. During this time the mixture was stirred and the temperature was maintained at 145°–155° C. By further processing of the reaction mixture, analogously to Example 1, the 1-aminoethane-1,1-diphosphonic acid was isolated and purified. The yield was 19.2 gm.

EXAMPLE 5

Into a mixture of 87.1 gm of butyric acid amide and 82 gm of phosphorous acid, hydrogen chloride gas was introduced therein for a period of 8 hours. During this time the mixture was stirred and the temperature was held at 150°–155° C. Subsequently the reaction mixture was cooled and was treated with water, whereby the 1-aminobutane-1,1-diphosphonic acid precipitated. The solid reaction product was filtered off, washed several times with water and dried. The yield was 83.3 gm.

EXAMPLE 6

Into a mixture of 143 gm of caprylic acid amide and 82 gm of phosphorous acid, hydrogen chloride gas was introduced for 8 hours. During this time the mixture was stirred and the temperature was held at 160° C. From the cooled reaction mixture, the 1-aminooctane-1,1-diphosphonic acid was precipitated by the addition of water. In order to remove any impurities from the solid product, this product was treated several times with half-concentrated hydrochloric acid, then washed with water and subsequently dried. The yield was 107 gm.

EXAMPLE 7

Into a mixture of 199 gm of lauric acid amide and 82 gm of phosphorous acid, hydrogen chloride gas was introduced for 8 hours. During this time the mixture was stirred and the temperature was maintained at 160° C. The reaction mixture was then cooled to room temperature and water was added. The precipitated 1- aminododecane-1,1-diphosphonic acid was suctioned off and dried. The yield was 123 gm.

EXAMPLE 8

Into a mixture of 127 gm of palmitic acid amide and 41 gm of phosphorous acid, hydrogen chloride gas was introduced for 8 hours. During this time the mixture was stirred and the temperature was held at 160° C. The 1-aminohexadecane-1,1-diphosphonic acid was precipitated by the addition of water to the cooled reaction mixture. Slight impurities were removed by treatment with half-concentrated hydrochloric acid. The yield was 72 gm.

EXAMPLE 9

Into a mixture of 87 gm of isobutyric acid amide and 82 gm of phosphorous acid, hydrogen chloride gas was introduced for 8 hours. During this time the mixture was stirred and the temperature was held at 155°–160° C. By further processing of the reaction mixture analogously to Example 1, the 1-amino-2-methylpropane-1,1-diphosphonic acid was isolated and purified. The yield was 8 gm.

EXAMPLE 10

Into a mixture of 87 gm of N-ethylacetamide and 82 gm of phosphorous acid, hydrogen chloride was introduced for 8 hours. During this time the mixture was stirred and the temperature was held at 150°–160° C. The reaction mixture was then treated analogously to Example 1, and the N-ethyl-1-aminoethane-1,1-diphosphonic acid product was obtained. The yield was 36.5 gm.

EXAMPLE 11

Into a mixture of 149 gm of hydrocinnamic acid amide and 82 gm of phosphorous acid, hydrogen chloride was introduced for 8 hours. During this time the mixture was stirred and the temperature held at 160° C. Subsequently the reaction mixture was treated with water. The aqueous solution was treated with a cation exchange resin in the H-form. The eluate was concentrated and the 1-amino-3-phenyl-propane-1,1-diphosphonic acid was precipitated with acetone. The yield was 39 gm.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. Process for the preparation of 1-aminoalkane-1,1-diphosphonic acids of the formula

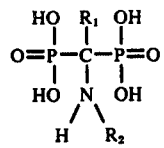

in which $R_1$ represents a member selected from the group consisting of alkyl with 1 to 20 carbon atoms, phenyl, phenylalkyl with 7 to 12 carbon atoms, alkylphenyl with 7 to 12 carbon atoms, and in which $R_2$ represents a member selected from the group consisting of hydrogen and alkyl with 1 to 4 carbon atoms, consisting essentially of reacting at a temperature of 100° to 170° C adducts of a hydrogen halide selected from the group consisting of HCl and HBr to a corresponding carboxylic acid amide of the formula

wherein $R_1$ and $R_2$ have the above-assigned meanings, with phosphorous acid, in the molar ratio of carboxylic acid amide: phosphorous acid of 1:0.5 to 1:3; and recovering said 1-aminoalkane-1,1-diphosphonic acids.

2. The process of claim 1 wherein the adducts of hydrogen halide and carboxylic acid amide are reacted with phosphorus acid at a temperature of 140° to 160° C.

3. The process of claim 1 wherein $R_1$ is alkyl with 4 to 20 carbon atoms.

4. Process for the preparation of 1-aminoalkane-1,1-diphosphonic acids of the formula

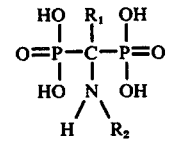

in which $R_1$ represents a member selected from the group consisting of alkyl with 1 to 20 carbon atoms, phenyl, phenylalkyl with 7 to 12 carbon atoms, alkylphenyl with 7 to 12 carbon atoms, and in which $R_2$ represents a member selected from the group consisting of hydrogen and alkyl with 1 to 4 carbon atoms, consisting essentially of reacting at a temperature of 100° to 170° C a hydrogen halide selected from the group consisting of HCl and HBr with a corresponding carboxylic acid amide of the formula

wherein $R_1$ and $R_2$ have the above-assigned meanings, and with phosphorous acid, in the molar ratio of carboxylic acid amide: phosphorous acid of 1:0.5 to 1:3, said reaction forming adducts of said hydrogen halide and said carboxylic acid amide in the reaction mixture; and recovering said 1-aminoalkane-1,1-diphosphonic acids.

* * * * *